(12) United States Patent
Lee et al.

(10) Patent No.: US 11,642,493 B2
(45) Date of Patent: May 9, 2023

(54) STEERABLE GUIDEWIRE AND METHOD FOR MANUFACTURING STEERABLE GUIDEWIRE, STEERABLE CATHETER AND METHOD FOR MANUFACTURING STEERABLE CATHETER

(71) Applicant: Korea Advanced Institute of Science And Technology, Daejeon (KR)

(72) Inventors: Doo Yong Lee, Daejeon (KR); Seung Gyu Kang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 535 days.

(21) Appl. No.: 16/560,702

(22) Filed: Sep. 4, 2019

(65) Prior Publication Data

US 2020/0238053 A1   Jul. 30, 2020

(30) Foreign Application Priority Data

Sep. 6, 2018   (KR) ......................... 10-2018-0106474
Aug. 16, 2019   (KR) ......................... 10-2019-0100129

(51) Int. Cl.
  *A61M 25/01*   (2006.01)
  *A61M 25/00*   (2006.01)
  (Continued)

(52) U.S. Cl.
  CPC .... *A61M 25/0127* (2013.01); *A61M 25/0009* (2013.01); *A61M 25/09* (2013.01);
  (Continued)

(58) Field of Classification Search
  CPC .......... A61M 25/0127; A61M 25/0009; A61M 25/09041; A61M 2025/09108;
  (Continued)

(56) References Cited

U.S. PATENT DOCUMENTS 5,353,807 A   10/1994  DeMarco
8,190,238 B2   5/2012  Moll et al.
(Continued)

FOREIGN PATENT DOCUMENTS

KR   101828289 B1   2/2018
KR   101860906 B1   5/2018

OTHER PUBLICATIONS

Seung Gyu Kang and Doo Yong Lee, "Specification of the bending of steerable guidewire for vascular intervention," Proceedings of the Korean Society of Mechanical Engineering (KSME) Annuals Spring Conference, May 2018, pp. 24-25.
(Continued)

*Primary Examiner* — Amber R Stiles
(74) *Attorney, Agent, or Firm* — Foley & Lardner LLP

(57) ABSTRACT

The present invention discloses a steerable guidewire and a method for manufacturing the same, and a steerable catheter and a method for manufacturing the same. According to an aspect of the present invention, a steerable guidewire, which is inserted into a catheter and guides the catheter to a desired blood vessel, may include: a steerable tip part that can be bent in at least two stages due to a stimulus from the outside and that is steered in a predetermined direction; and a non-steerable tip part that is not steerable. The steerable tip part may include: a first steerable tip part having a first length and bent in a first angle with respect to the non-steerable tip part; and a second steerable tip part having one end connected to the first steerable tip part, having a second length, and bent and steered into a second angle with respect to the non-steerable tip part. The first steerable tip part may be positioned farther from the non-steerable tip part than the second steerable tip part. The first length of the first steerable tip part may be smaller than a sum of lengths of steerable tip
(Continued)

parts other than the first steerable tip part, and the first angle may be steered so as to be larger than the second angle.

14 Claims, 13 Drawing Sheets

(51) Int. Cl.
    *A61M 25/09*     (2006.01)
    *B29C 41/02*     (2006.01)
    *B29C 33/38*     (2006.01)
    *B29K 83/00*     (2006.01)
    *B29L 31/00*     (2006.01)

(52) U.S. Cl.
    CPC ... *A61M 25/09041* (2013.01); *B29C 33/3842* (2013.01); *B29C 41/02* (2013.01); *A61M 2025/09108* (2013.01); *A61M 2025/09141* (2013.01); *A61M 2025/09175* (2013.01); *A61M 2205/0266* (2013.01); *A61M 2205/0283* (2013.01); *A61M 2205/3317* (2013.01); *A61M 2205/3368* (2013.01); *B29K 2083/00* (2013.01); *B29K 2855/02* (2013.01); *B29L 2031/7542* (2013.01)

(58) Field of Classification Search
    CPC ........... A61M 2025/09141; A61M 2205/0266; A61M 2205/0283; A61M 2205/3317; A61M 2205/3368; A61M 25/0138; A61M 25/0158; A61M 2025/09133; A61M 25/09; A61M 25/008; A61M 25/0133; A61M 25/0147; A61M 2025/0079; A61M 2025/0161; B29C 33/3842; B29C 41/02; B29K 2083/00; B29K 2855/02; B29L 2031/7542

See application file for complete search history.

(56) References Cited

U.S. PATENT DOCUMENTS

2005/0113862 A1\*   5/2005  Besselink ............. A61M 25/04
                                                                 606/200
2006/0116633 A1   6/2006  Shachar

OTHER PUBLICATIONS

Office Action dated Nov. 28, 2020 in counterpart Korean Appl. 10-2019-0100129 (8 pgs.).

\* cited by examiner

[Fig. 1]
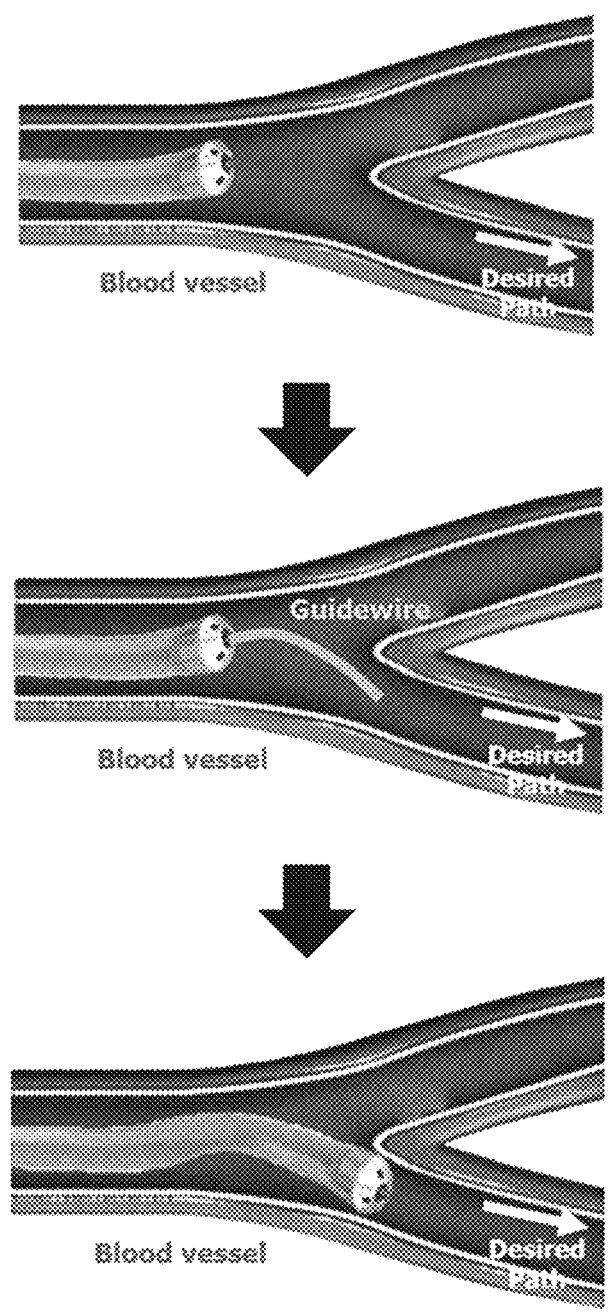

[Fig. 2]
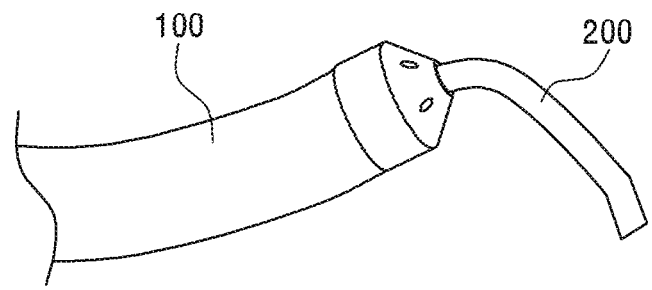
(a)
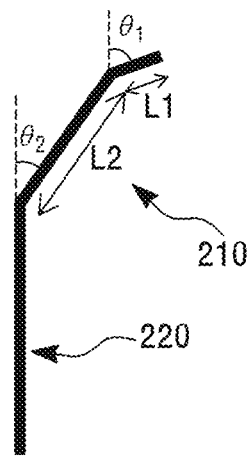
(b)
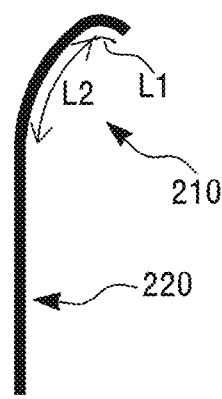
(c)

[Fig. 3]
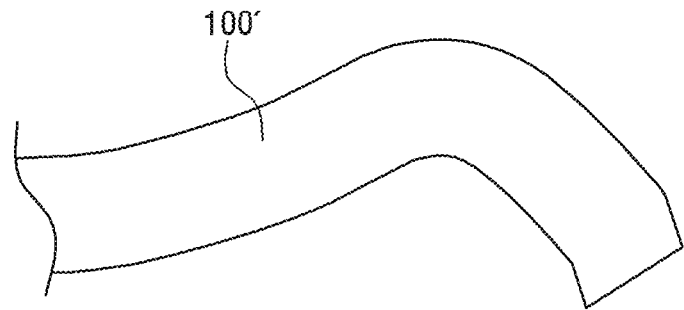
(a)
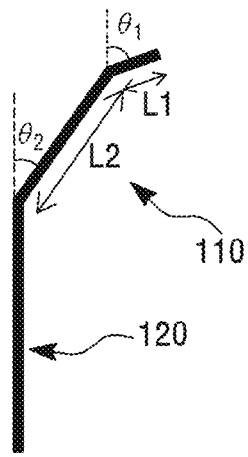
(b)
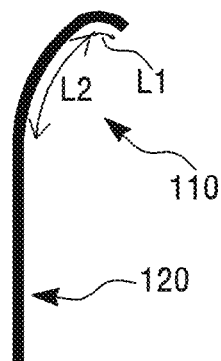
(c)

[Fig. 4]
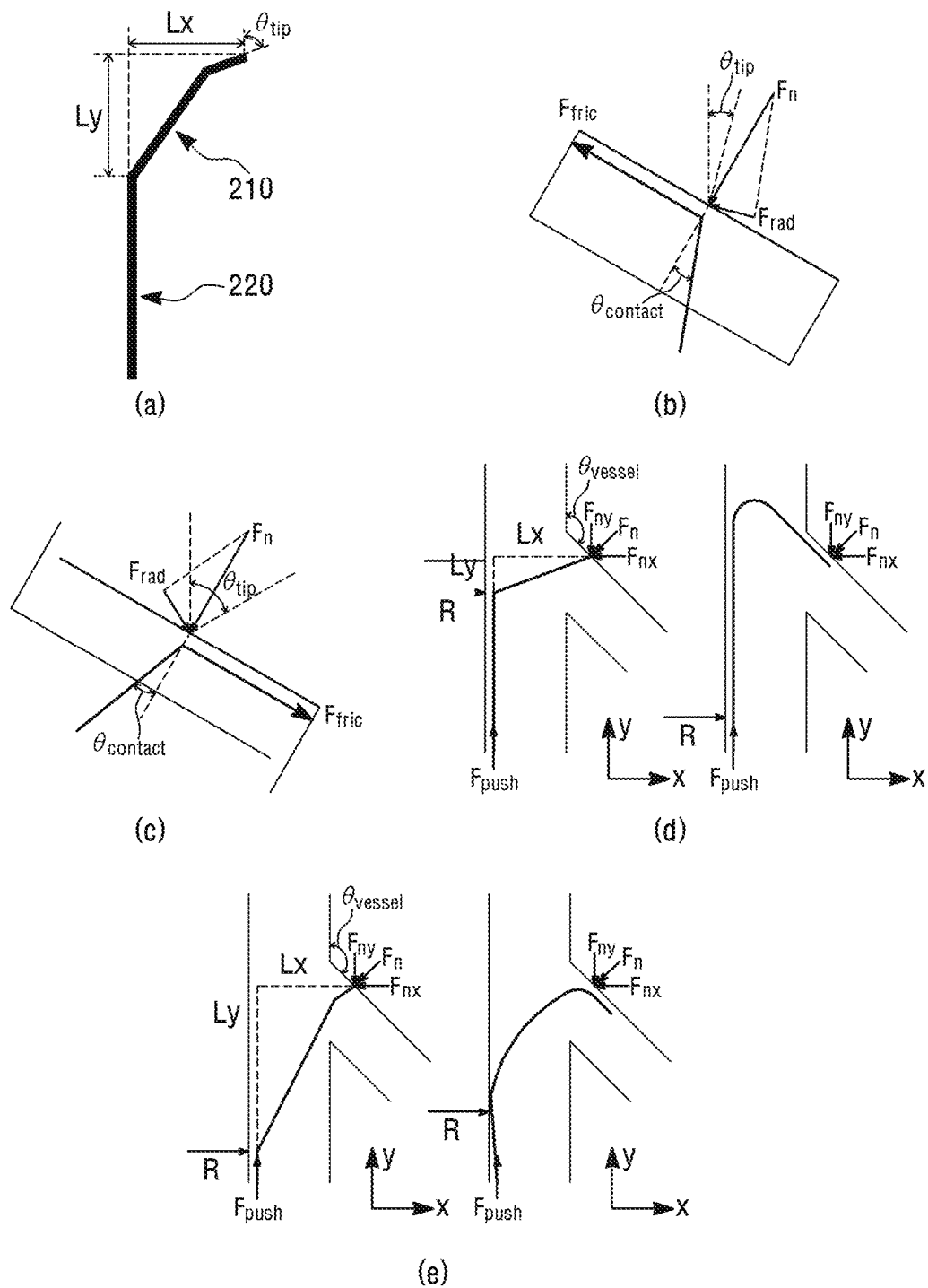

[Fig. 5]
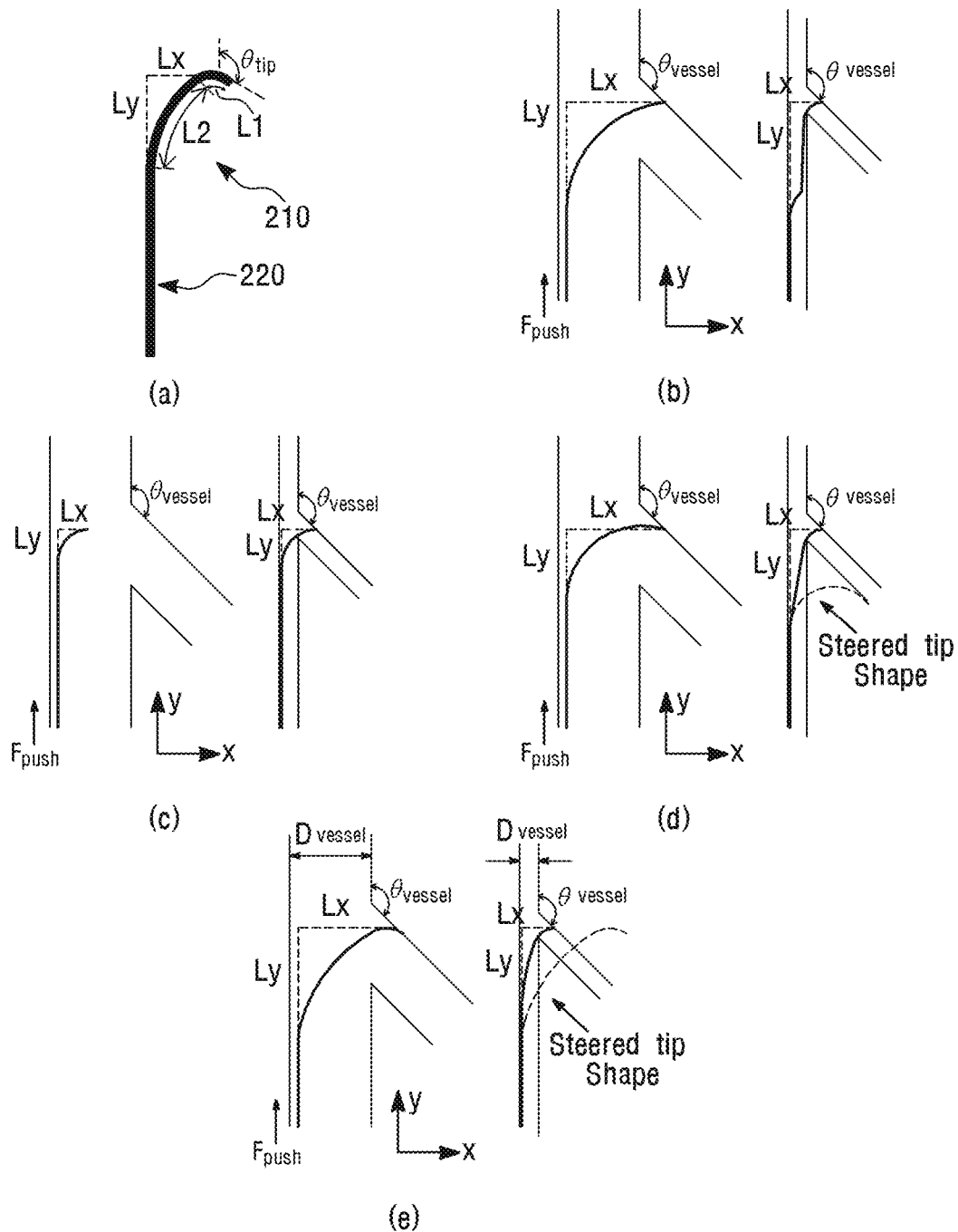

[Fig. 6]
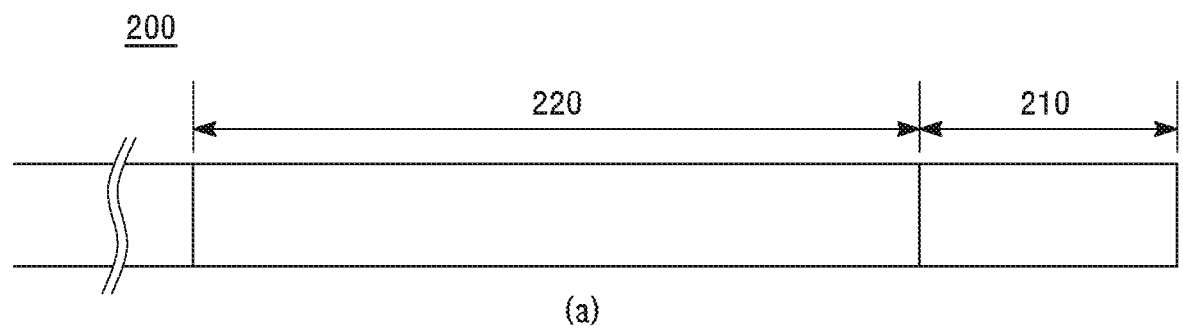
(a)
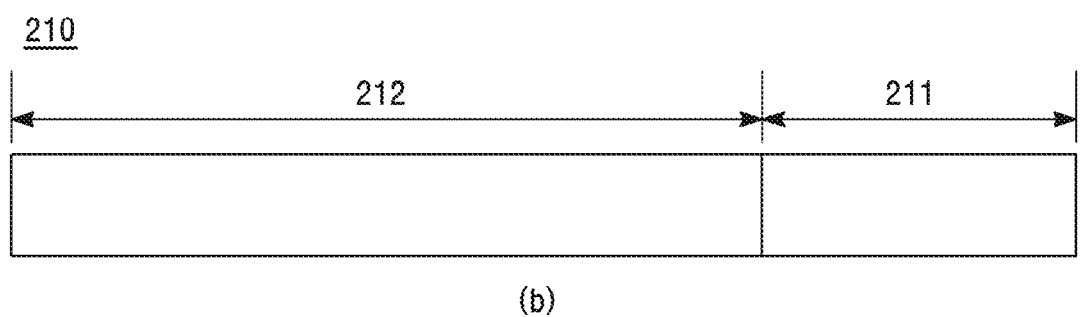
(b)
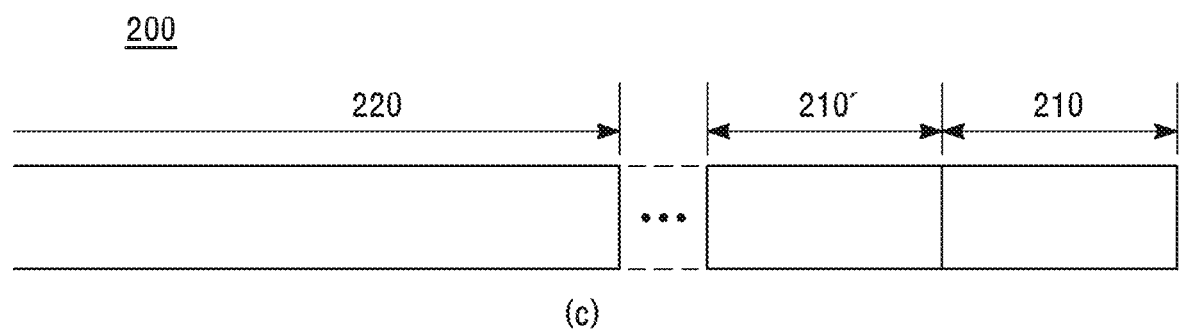
(c)

[Fig. 7]
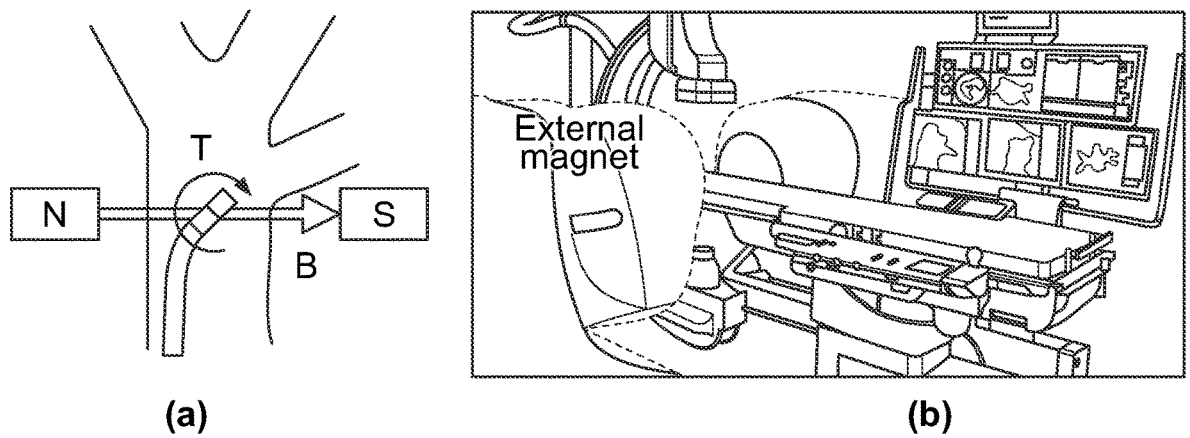
(a)  (b)
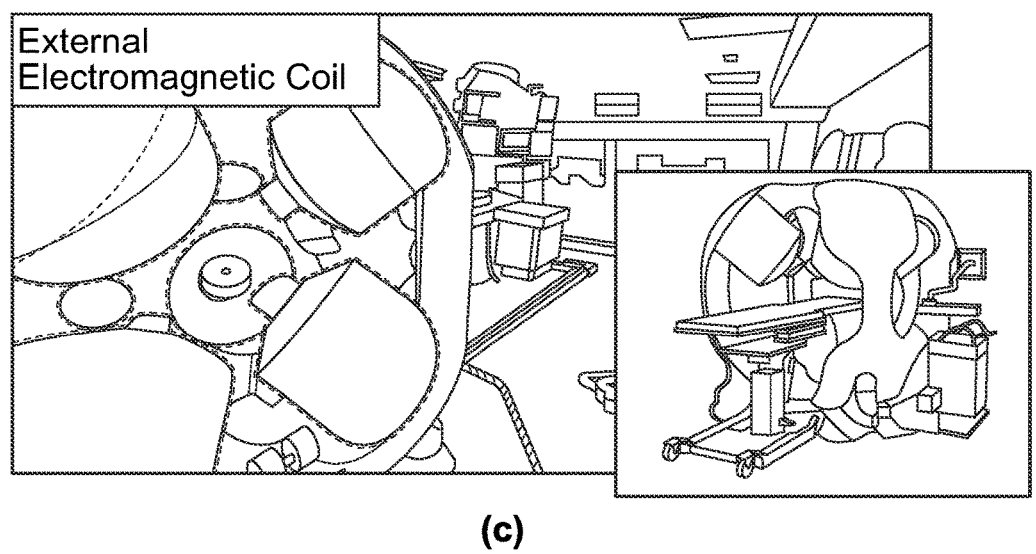
(c)
[Fig. 8]
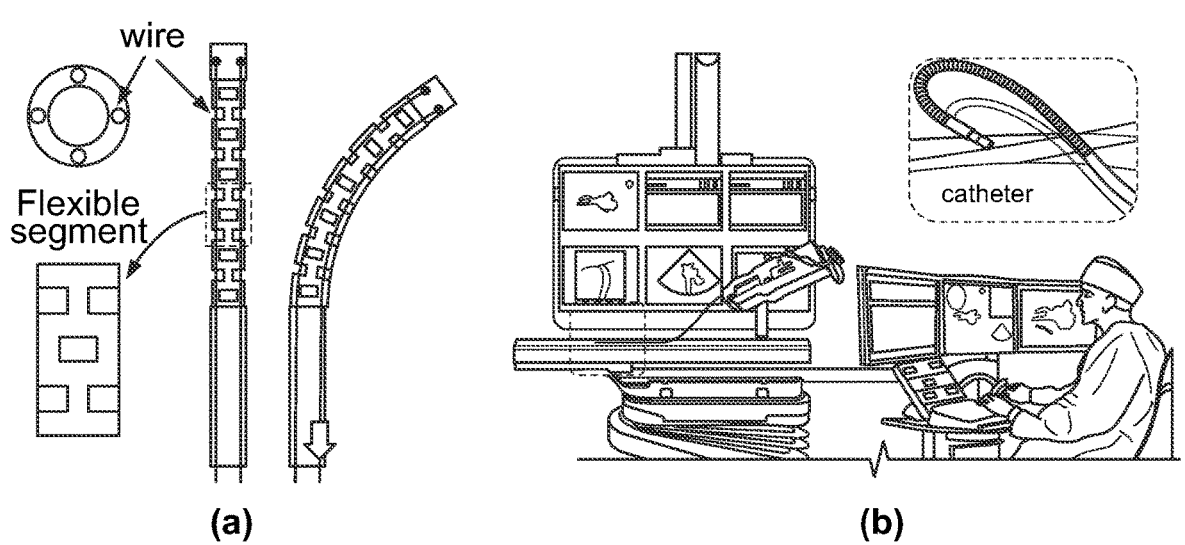
(a)  (b)

[Fig. 9]
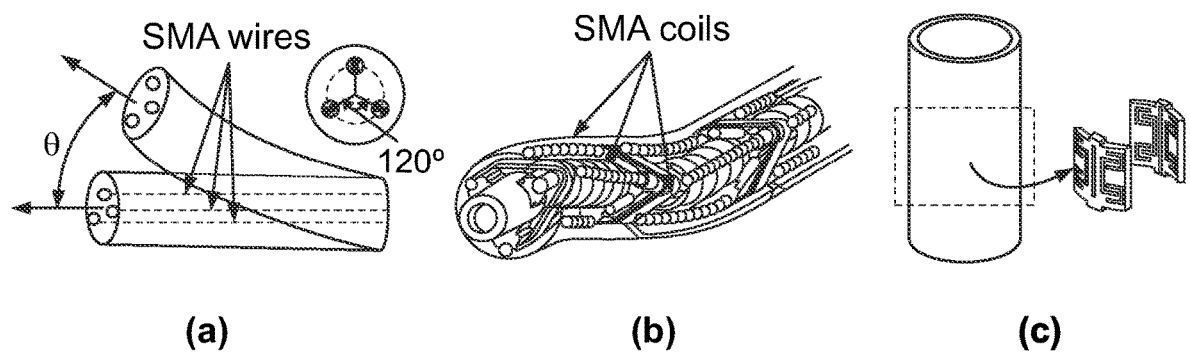
[Fig. 10]
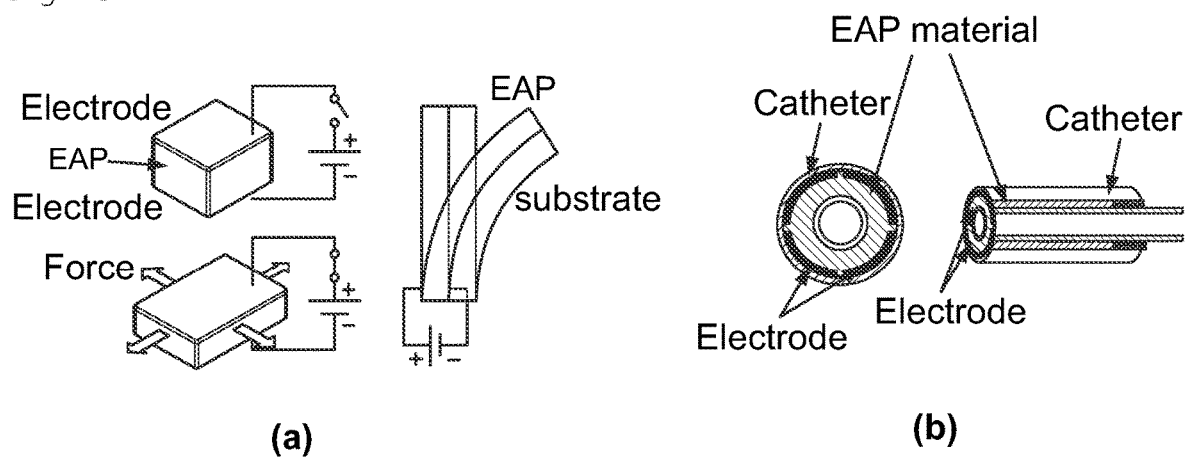

[Fig. 11]
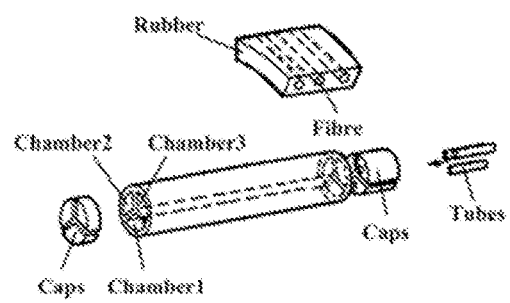
(a)
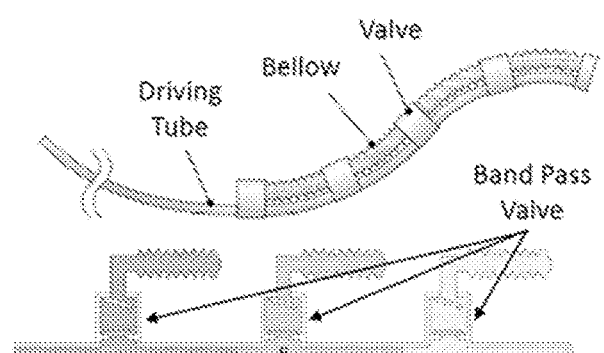
(b)

[Fig. 12]
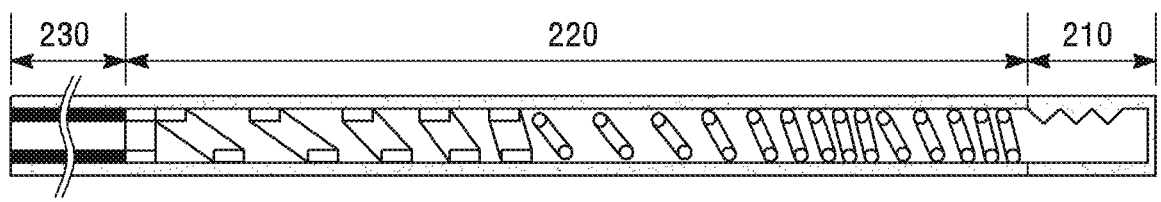

[Fig. 13]
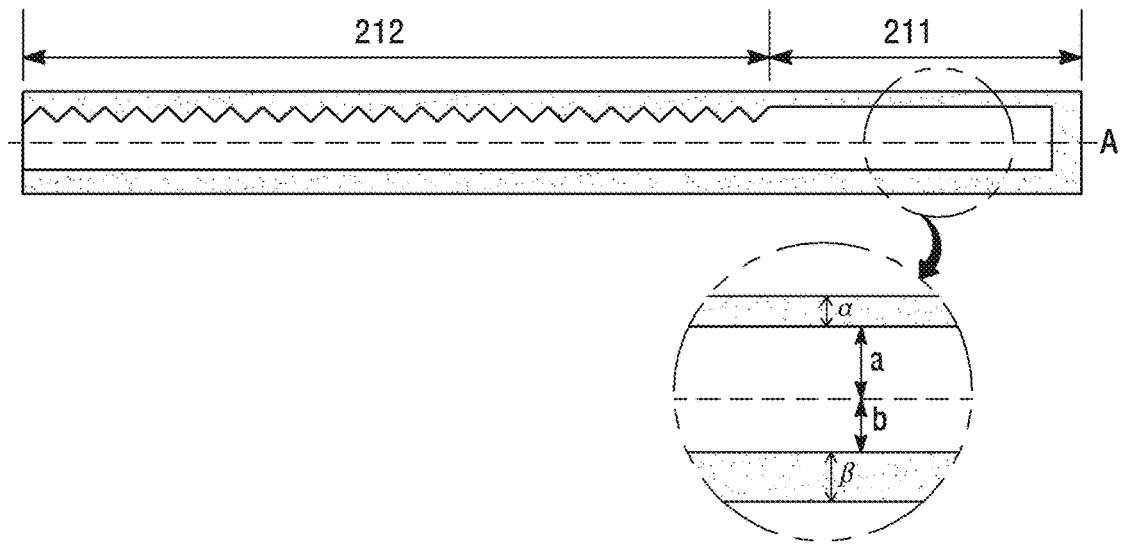
[Fig. 14]
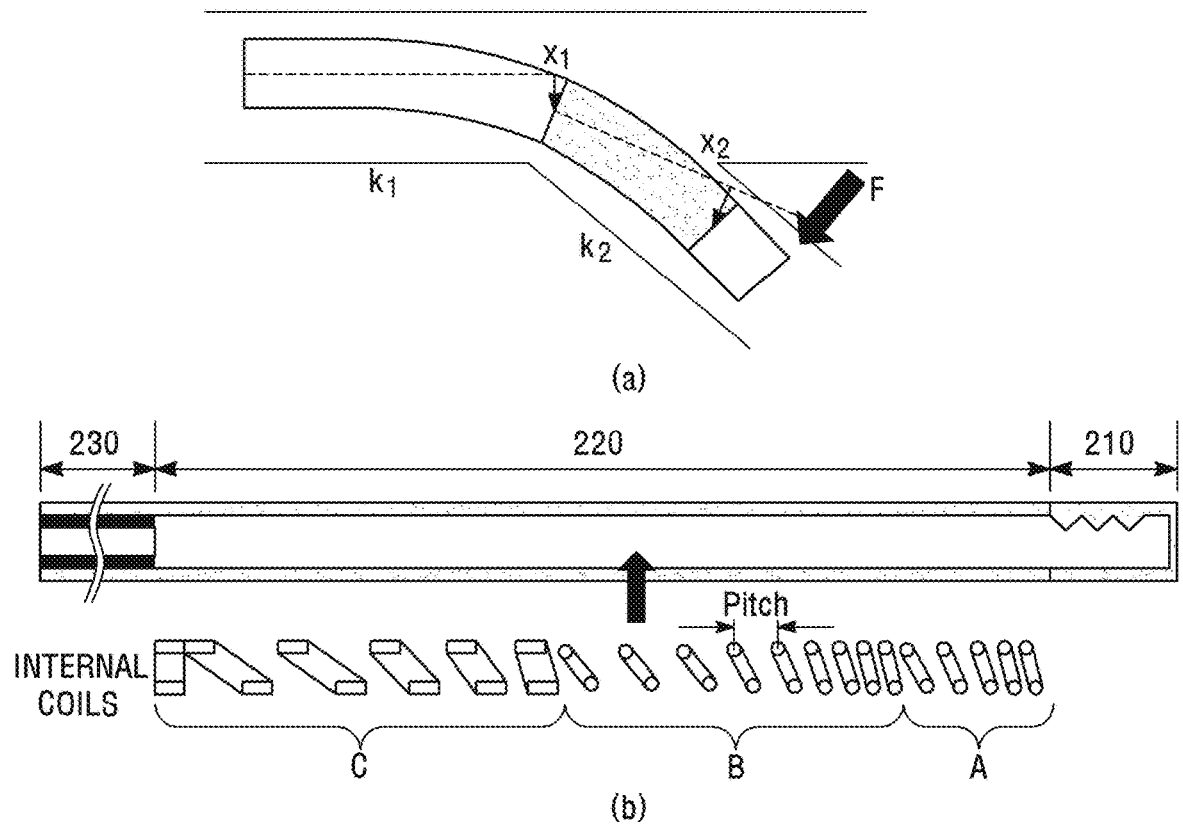

[Fig. 15]
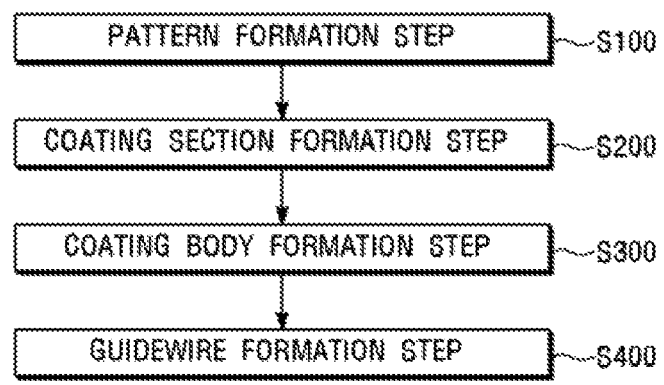

[Fig. 16]
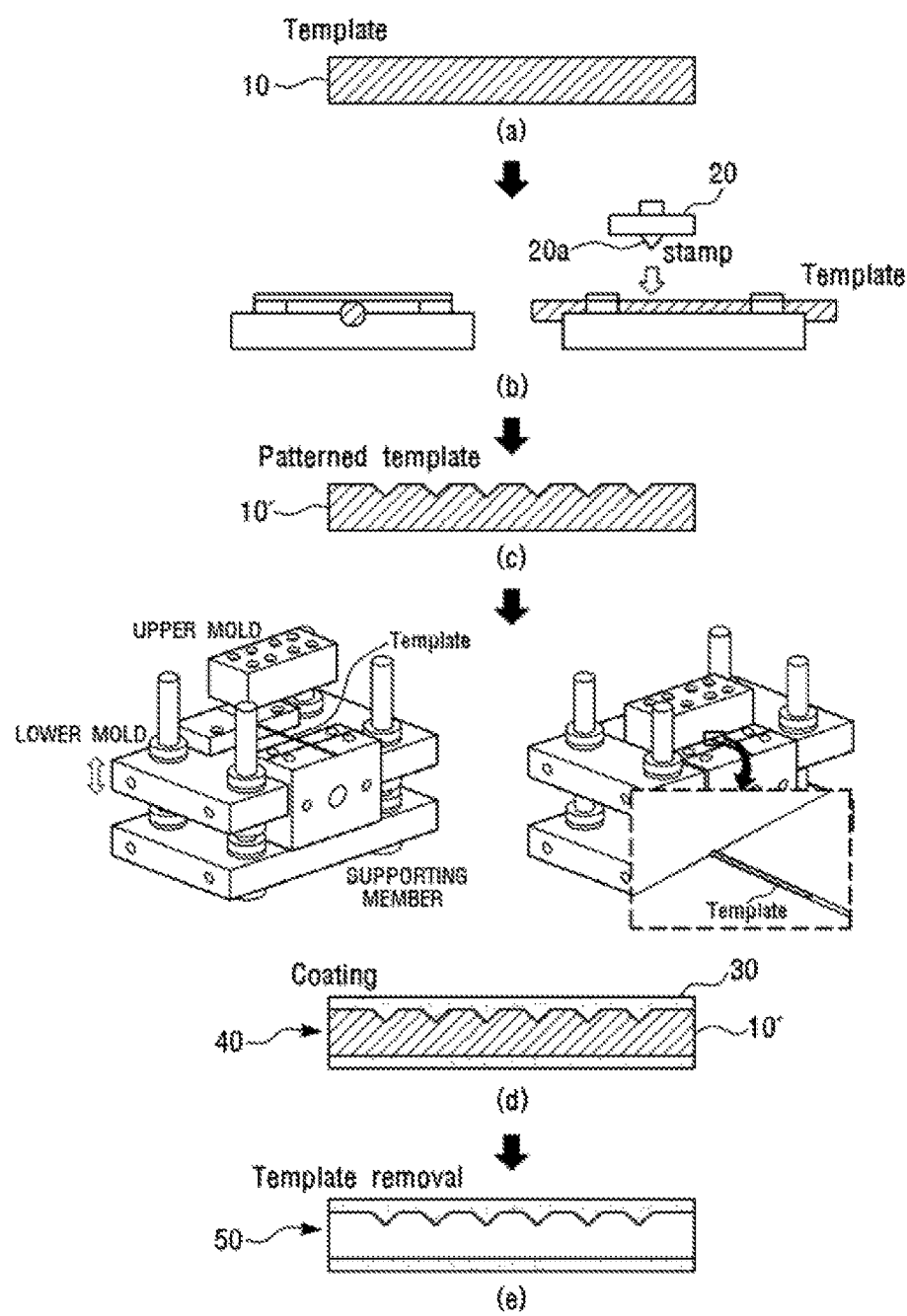

STEERABLE GUIDEWIRE AND METHOD FOR MANUFACTURING STEERABLE GUIDEWIRE, STEERABLE CATHETER AND METHOD FOR MANUFACTURING STEERABLE CATHETER

CROSS-REFERENCE TO RELATED APPLICATION

This application claims priority to Korean Patent Application No. 10-2018-0106474 filed on Sep. 6, 2018, and to Korean Patent Application No. 10-2019-0100129 filed on Aug. 16, 2019 and all the benefits accruing therefrom under 35 U.S.C. § 119, the contents of which are incorporated by reference in their entirety.

BACKGROUND

The present disclosure relates to a catheter, and more particularly, to a steerable guidewire provided with a tip part deformed in a bent shape of two or more stages, and a method for manufacturing the same, and to a steerable catheter and a method for manufacturing the same.

Vascular intervention treatment is the treatment for diagnosing and treating a disease by inserting a catheter that is a treatment tool having a guide tube shape reaching the inside of a blood vessel under image guidance. A doctor forms a small hole in the neck, an ankle, or an inguinal area, inserts a catheter into a blood vessel through the hole, and leads the catheter tip part to approach a target lesion under image guidance. When the catheter tip part reaches a target blood vessel portion, a medicine is injected through an inner tube or a treatment tool is inserted to perform diagnosis or treatment.

For the treatment, it is important to lead the catheter to reach a target position inside a blood vessel, but it is not easy to selectively insert the catheter in a desired direction due to the characteristics of the blood vessel having many branches. Thus, a guidewire which is a treatment tool having a thin metal wire shape is used together.

FIG. 1 is a view illustrating a selective insertion method using an existing guidewire.

Referring to FIG. 1, when encountering a blood vessel branch, a guidewire is inserted through a catheter inner tube after shaping the tip part of the guidewire to conform to the shape of a blood vessel. When the guidewire reaches the catheter tip part, the guidewire is first advanced by using the shaped form, selective insertion is enabled by a method of advancing the catheter over the guidewire.

However, in case of existing guidewires, there is a limitation that the shape of the tip part should manually be changed according to the shape of a blood vessel branch. A blood vessel, in which various diameters and angles are formed for each branch, may be damaged when the guidewire is excessively shaped to be remarkably deviated from the shape of the blood vessel, and when the shaping is not sufficient, selective insertion into a desired blood vessel becomes difficult. Thus, when the shapes of the blood vessel branches up to a target position are diversified, the guidewire should be shaped several times, and the guidewire should be extracted to the outside for each time of the shaping, which serves as an important factor of increasing a treatment time.

In order to solve the limitation of such existing guidewires, research for an actively steerable catheter or a guidewire has been carried out. Driving methods by using electricity, heat, a magnetic field, pressure, and a wire were proposed as a mechanism for steering the tip part of a catheter or a guidewire, and degrees of freedom were developed from a single degree of freedom up to multiple degrees of freedom according to a target treatment. When the steering degree of freedom increases, various shapes conforming to the shape of a blood vessel may be formed. Therefore, there is an advantage of easy selective insertion, but there is a disadvantage of difficulty in miniaturization due to a complicated structure. Thus, a steerable catheter or guidewire developed in multiple degrees of freedom has a relatively large size compared to that in case of a single degree of freedom, and therefore there is a limitation of difficulty in application up to a fine blood vessel.

RELATED ART DOCUMENTS

Patent Document (Patent document 1) U.S. Pat. No. 5,353,807, filed on Oct. 11, 1994

(Patent document 1) U.S. Patent Publication No. US 2006/0116633 A1, published on Jun. 1, 2006

(Patent document 3) U.S. Pat. No. 8,190,238, filed on May 29, 2012

SUMMARY

The present disclosure provides a steerable guidewire in which a steerable tip part of a guidewire is deformed in a bent shape of at least two stages due to an external stimulus and is allowed to be steered in a predetermined direction, a method for manufacturing the steerable guidewire, a steerable catheter, and a method for manufacturing the steerable catheter.

However, the object of the present disclosure is not limited to the aforesaid objects and may be variously expanded without departing from the spirit and scope of the present disclosure.

In accordance with an exemplary embodiment of the present invention, a steerable guidewire, which is inserted into a catheter and guides the catheter to a desired blood vessel, includes: a steerable tip part that can be bent in at least two stages due to a stimulus from the outside and that is steered in a predetermined direction; and a non-steerable tip part that is not steerable. The steerable tip part may include: a first steerable tip part having a first length and bent in a first angle with respect to the non-steerable tip part; and a second steerable tip part of which one end is connected to the first steerable tip part, the second steerable tip part having a second length, and bent and steered into a second angle with respect to the non-steerable tip part. The first steerable tip part may be positioned farther from the non-steerable tip part than the second steerable tip part. The first length of the first steerable tip part may be smaller than a sum of lengths of steerable tip parts other than the first steerable tip part, and the first angle may be steered so as to be larger than the second angle.

In addition, the steerable tip part may have a single degree of freedom and be bent in a shape of at least two stages.

In addition, the steerable tip part may be steered in shapes of Equations 1, 2, and 3 below.

$$\theta_{tip} > \theta_{vessel} - 90 \qquad [\text{Equation 1}]$$

$$Ly > Lx \qquad [\text{Equation 2}]$$

$$Lx > D_{vessel} \qquad [\text{Equation 3}]$$

(Lx, Ly: lengths of the steerable guidewire in an x-direction and a y-direction with respect to a bent section from one end to the other end of the steerable tip part, $\theta_{tip}$: an angle of an end, that is, the other end of the steerable guidewire, $D_{vessel}$: a diameter of a blood vessel)

In accordance with another exemplary embodiment of the present invention, a steerable guidewire, which is inserted into a catheter and guides the catheter to a desired blood vessel, includes: a steerable tip part that can be bent in at least two stages due to a stimulus from the outside and that is steered in a predetermined direction; and a non-steerable tip part that is not steerable. The steerable tip part may include: a first steerable tip part having a first length and bent so as to have a first bending radius; and a second steerable tip part having one end connected to the first steerable tip part and the other end connected the non-steerable tip part, having a second length, and bent and steered so as to have a second bending radius, wherein the first steerable tip part may be positioned farther from the non-steerable tip part than the second steerable tip part. The first length may be smaller than the second length, and the first bending radius may be smaller than the second bending radius.

In addition, the steerable tip part may have a tubular shape and be formed in a non-symmetrical structure with respect to a center axis line of the inside thereof.

In addition, in the steerable tip part, a distance from the center axis line to a first inner circumferential surface may be larger than a distance from the center axis line to a second inner circumferential surface facing the first inner circumferential surface.

In addition, the steerable tip part may be formed in at least two different structures in a lengthwise direction.

In addition, the steerable tip part may include a first steerable tip part and a second steerable tip part connected to the first steerable tip part, wherein the second steerable tip part may have a predetermined pattern form on one side therein.

In addition, the non-steerable tip part may have a structure in which bending stiffness increases as being farther from the steerable tip part.

In addition, the non-steerable tip part may have one or more coils positioned therein, wherein the one or more coils may each have an increasing pitch, increasing diameter, or simultaneously increasing pitch and diameter.

In accordance with still another exemplary embodiment of the present invention, a steerable catheter includes: a steerable tip part that can be bent in at least two stages due to a stimulus from the outside and that is steered in a predetermined direction; and a non-steerable tip part that is not steerable. The steerable tip part may include: a first steerable tip part having a first length and bent in a first angle with respect to the non-steerable tip part; and a second steerable tip part having one end connected to the first steerable tip part, having a second length, and bent and steered into a second angle with respect to the non-steerable tip part. The first steerable tip part may be positioned farther from the non-steerable tip part than the second steerable tip part. The first length of the first steerable tip part may be smaller than a sum of lengths of steerable tip parts other than the first steerable tip part, and the first angle may be steered so as to be larger than the second angle.

In accordance with yet another exemplary embodiment of the present invention, a method for manufacturing a steerable guidewire, which is inserted into a catheter and guides the catheter to a desired blood vessel, includes: a pattern formation step for forming an engraved pattern on one side of a cylindrical template using a stamp on which a predetermined embossed pattern is formed; a coating section formation step for forming a coating section by coating, with a flexible material, an outer circumferential surface of the template on which the engraved pattern is formed; a coating body formation step for curing the coating section and forming a coating body including the template on which the engraved pattern is formed and the coating section; and a guidewire formation step for removing, from the coating body, the template on which the engraved pattern is formed to form a steerable guidewire.

In addition, the predetermined embossed pattern may have an inverted triangle-shaped cross-section.

In addition, in the guidewire formation step, the template on which the engraved pattern is formed may be removed from the coating body by using a predetermined solvent, the solvent may be acetone that dissolves the template, and a material for the template may be ABS plastic.

In accordance with yet another exemplary embodiment of the present invention, a method for manufacturing a steerable catheter, includes: a pattern formation step for forming an engraved pattern on one side of a cylindrical template using a stamp on which a predetermined embossed pattern is formed; a coating section formation step for forming a coating section by coating, with a flexible material, an outer circumferential surface of the template on which the engraved pattern is formed; a coating body formation step for curing the coating section and forming a coating body including the template on which the engraved pattern is formed and the coating section; and a catheter formation step for removing, from the coating body, the template on which the engraved pattern is formed to form a steerable catheter.

BRIEF DESCRIPTION OF THE DRAWINGS

Exemplary embodiments can be understood in more detail from the following description taken in conjunction with the accompanying drawings, in which:

FIG. 1 is a view illustrating a selective insertion method using an existing guidewire;

FIG. 2 is a view illustrating a steerable guidewire in accordance with an exemplary embodiment of the present invention;

FIG. 3 is a view illustrating a steerable catheter in accordance with an exemplary embodiment of the present invention;

FIG. 4 is a view for describing a relationship between a branch angle of a blood vessel and a shape of a guidewire;

FIG. 5 is a view for describing a relationship between a diameter of a blood vessel and a shape of a guidewire;

FIG. 6 is a view illustrating a structure of a steerable guidewire in accordance with an exemplary embodiment of the present invention;

FIG. 7 is a view for describing a steering mechanism using magnetic induction;

FIG. 8 is a view for describing a steering mechanism using a wire;

FIG. 9 is a view for describing a steering mechanism using a shape memory alloy;

FIG. 10 is a view for describing a steering mechanism using an electrically activated polymer;

FIG. 11 is a view for describing a steering mechanism using pressure;

FIG. 12 is a view illustrating a steerable guidewire using pressure in accordance with an exemplary embodiment of the present invention;

FIG. 13 is a view illustrating a specific structure of the steerable tip part shown in FIG. 12;

FIG. 14 is a view illustrating a specific structure of the non-steerable tip part shown in FIG. 12;

FIG. 15 is a view illustrating a method for manufacturing a steerable guidewire in accordance with an exemplary embodiment of the present invention; and FIG. 16 is a view for describing steps for manufacturing the steerable guidewire of FIG. 15.

DETAILED DESCRIPTION OF EMBODIMENTS

The detailed description of the invention to be provided later refers to the accompanying drawings which exemplarily illustrates a specific embodiment in which the invention may be carried out. These embodiments will be described in sufficient detail to enable those skilled in the art to practice the invention. It is to be understood that various embodiments of the present invention are different from each other but need not to be mutually exclusive. For example, a specific shape, structure and characteristics disclosed in the present invention provided herein may be implemented in other embodiments without departing from the spirit and scope of the present invention in relation to one embodiment. In addition, it is to be understood that the position or arrangement of individual components in each disclosed embodiment may be modified without departing from the spirit and scope of the invention. Accordingly, the following detailed description is not intended to be taken in a limiting sense, and the scope of the present invention is to be limited only by the appended claims, along with all ranges equivalent to those claimed in the claims, if properly described. In the drawings, similar reference symbols indicate the same or similar function in many aspects.

Hereinafter, with reference to the accompanying drawings, a steerable guidewire and the method for manufacturing the same, and a steerable catheter and a method for manufacturing the same will be described according to exemplary embodiments of the present invention. In particular, the present invention proposes a novel structure in which the steerable tip part of a guidewire can be bent in at least two stages due to an external stimulus and is steered in a predetermined direction. In other words, the present invention intends to propose a steerable guidewire and a catheter which are capable of approaching a fine blood vessel. A single-degree-of-freedom steerable mechanism is proposed for miniaturization, and unlike the existing research in which a degree of freedom is increased for selective insertion into blood vessels with various shapes, it is intended to make selective insertion possible by changing a bent shape in a single degree of freedom.

FIG. 2 is a view illustrating a steerable guidewire in accordance with an exemplary embodiment of the present invention.

Referring to (a) of FIG. 2, a steerable guidewire according to an exemplary embodiment of the present invention may be inserted through an inner tube of a catheter and guide the catheter so as to be capable of being selectively inserted into a desired blood vessel. That is, the tip part of the steerable guidewire can be bent in at least two stages by an external stimulus and steered in a predetermined direction, and a catheter may be selectively inserted into a desired blood vessel by being advanced over the steerable guidewire. Here, the stimulus is a stimulus that can bend the tip part of the steerable guidewire in at least two stages, and may be a stimulus due to any one of, for example, a magnetic force, a force, a temperature, a voltage, or a pressure.

At this point, the tip part of the guidewire is roughly defined as two portions according to whether to be steered, and may be defined as a steerable tip part that is steered and a non-steerable tip part that is not steered.

Referring to (b) of FIG. 2, a steerable guidewire according to an exemplary embodiment of the present invention may include a steerable tip part 210 and a non-steerable tip part 220, and the steerable tip part 210 may include: a first steerable tip part having a first length L1 and bent in a first angle $\theta 1$ in a straight-line shape with respect to the non-steerable tip part; and a second steerable tip part having one end connected to the first steerable tip part 210 and the other end connected to the non-steerable tip part 220, having a second length, and bent and steered in a second angle $\theta 2$ in a straight-line shape with respect to the non-steerable tip part 220. Here, the first length L1 is favorably formed to be smaller than the second length L2, and the first angle $\theta 1$ is favorably formed to be larger than the second angle $\theta 2$.

Referring to (c) of FIG. 2, a steerable guidewire according to an exemplary embodiment of the present invention may include a steerable tip part 210 and a non-steerable tip part 220, and the steerable tip part 210 may include: a first steerable tip part having a first length L1 and bent in a curved shape so as to have a first bending radius R1; and a second steerable tip part having one end connected to the first steerable tip part 210 and the other end connected to the non-steerable tip part 220, having a second length L2, and bent and steered in a curved shape so as to have a second bending radius R2. Here, the first length L1 is favorably formed to be smaller than the second length L2, and the first bending radius R1 is favorably formed to be smaller than the second bending radius R2.

At this point, the steerable tip part 210 may be formed in a bent shape of at least two stages in a single degree of freedom. In addition, the steerable tip part 210 may be controlled to be in a bent shape of at least two stages in at least two degrees of freedom. In addition, the steerable tip part 210 may have a workspace limited to be in a bent shape of at least two stages in at least two degrees of freedom.

FIG. 3 is a view illustrating a steerable catheter in accordance with an exemplary embodiment of the present invention.

Referring to (a) FIG. 3, a steerable catheter 100' according to an exemplary embodiment of the present invention may be selectively inserted into a desired blood vessel by itself without using a guidewire. That is, a tip part of the steerable catheter 100' can be bent in at least two stages due to an external stimulus and is steered in a predetermined direction, and may selectively be inserted into a desired blood vessel.

At this point, the tip part of the steerable catheter is roughly defined as two portions according to whether to be steered, and may be defined as a steerable tip part that is steered and a non-steerable tip part that is not steered.

Referring to (b) of FIG. 3, a steerable catheter 100' according to an exemplary embodiment of the present invention may include a steerable tip part 110 and a non-steerable tip part 120, and the steerable tip part 110 may include: a first steerable tip part having a first length L1 and bent in a first angle $\theta 1$ with respect to the non-steerable tip part 120; and a second steerable tip part having one end connected to the first steerable tip part 110 and the other end connected to the non-steerable tip part 120, having a second length L2, and bent and steered in a second angle $\theta 2$ with respect to the non-steerable tip part 120. Here, the first length L1 is favorably formed to be smaller than the second length L2, and the first angle $\theta 1$ is favorably formed to be larger than the second angle $\theta 2$.

At this point, when the steerable tip part 110 is implemented so as to further include an additional steerable tip part aside from the first steerable tip part and the second steerable tip part, the first length of the first steerable tip part is formed to be smaller than the sum of the lengths of steerable tip parts other than the first steerable tip part.

Referring to (c) of FIG. 3, a steerable catheter 100' according to an exemplary embodiment of the present invention may include a steerable tip part 110 and a non-steerable tip part 120, and the steerable tip part 110 may include: a first steerable tip part having a first length L1 and bent in a curved shape so as to have a first bending radius R1; and a second steerable tip part having one end connected to the first steerable tip part 110 and the other end connected to the non-steerable tip part 120, having a second length L2, and bent and steered in a curved shape so as to have a second bending radius R2. Here, the first length L1 is favorably formed to be smaller than the second length L2, and the first bending radius R1 is favorably formed to be smaller than the second bending radius R2.

The steerable catheter formed as such has the same structure and the same operation principle as the steerable guidewire described in FIG. 2, and thus, only the steerable guidewire will be hereinafter described as an example.

A bending phenomenon of such a steerable guidewire is determined on the basis of the structural characteristics of a blood vessel, and factors, among the structural characteristics of the blood vessel, which affect the insertion of the guidewire, are diameters and branch angles.

First, the branch angle of a blood vessel which affects the insertion of the steerable guidewire will be described. In case of a small branch angle, when the guidewire is pushed and inserted while the tip part thereof enters the corresponding branch, the guidewire may selectively be inserted, but when the branch angle increases, the guidewire may selectively be inserted into a desired branch only when the shape of the guidewire satisfies additional conditions.

FIG. 4 is a view for describing a relationship between a branch angle of a blood vessel and a shape of a guidewire.

Referring to (a) of FIG. 4, in a steerable guidewire according to an exemplary embodiment of the present invention, Lx is defined as the length of a bent section of a tip part from one end section to the other end in an x-axis direction, Ly is defined as the length in a y-axis direction, and $\theta_{tip}$ is defined as the angle of an end of the guidewire, that is, the angle of the other end.

At this point, Ly is the length of a side vertically extending from a cross-section on one end among the two sides of a right triangle, which has, as the hypotenuse, a line connecting one end and the other end of the steerable tip part, and Lx is the length of the remaining side, that is, the length of the side extending from the other end.

Referring to (b) and (c) of FIG. 4, when the guidewire is to be inserted into a blood vessel having a blood vessel angle $\theta_{vessel}$, two cases may occur according to an angle $\theta_{contact}$ formed by the tip part of the guidewire and a line perpendicular to the blood vessel wall. That is, as shown in (b) of FIG. 4, when the tip part of the guidewire is inclined counterclockwise from a line perpendicular to the blood vessel wall and $\theta_{contact}$ is negative, Frad is in a direction outward from the blood vessel, and therefore the guidewire is pushed out of the blood vessel. Conversely, as shown in (c) of FIG. 4, when the tip part of the guidewire is inclined clockwise from a line perpendicular to the blood vessel wall and $\theta_{contact}$ is positive, $F_{rad}$ which is a side-surface-direction component force of $F_n$ acting to the guidewire is in a direction into the blood vessel, and therefore the guidewire advances into the blood vessel.

Thus, when expressing the condition of θtip for selective insertion, following Equation 1 is obtained.

$$\theta_{tip} > \theta_{vessel} - 90 \quad \text{[Equation 1]}$$

Referring to (d) of FIG. 4, in case of single bending, even when $\theta_{contact}$ is positive, Lx is greater than Ly, and therefore a prolapsed phenomenon occurs in which the guidewire may not be inserted into a desired blood vessel but may be deviated.

Referring to (e) of FIG. 4, in case of two-stage bending, since Lx may be configured to be greater than Lx while $\theta_{contact}$ is positive, the guidewire may selectively be inserted into a desired blood vessel.

Thus, when expressing the condition of Lx and Ly for selective insertion, following Equation 2 is obtained.

$$Ly > Lx \quad \text{[Equation 2]}$$

In addition, the diameter of a blood vessel is also a factor among important factors which determines the bending shape of the guidewire. Since the purpose is to reach a target lesion through a single guidewire, the guidewire should selectively be inserted into all blood vessels from large blood vessels to small blood vessels.

FIG. 5 is a view for describing a relationship between a diameter of a blood vessel and a shape of a guidewire.

Referring to (a) of FIG. 5, since a mechanism applied to a steerable guidewire is bent mainly in a curved shape having a constant radius of curvature or a constant bending radius, a bending section may be generated in a curved shape having mutually different bending radii in a two-stage bent shape.

Referring to (b) of FIG. 5, when the angle of a steerable tip part is satisfied in order to selectively insert a guidewire into a large-diameter blood vessel, the guidewire may be inserted even with single bending. However, when the same steerable tip part is applied to a case of a small blood vessel, a smaller bending radius is required because the same angle should be formed at the steerable tip part with a small length. Thus, as expressed by "steered tip shape" in the drawing on the right side, the steerable tip part should be further bent to be fitted to the shape of the blood vessel. At this point, when the tip part is soft, stress concentration may occur due to excessive deformation and the tip part is not easily selectively inserted due to adhesion to a blood vessel wall, and when the tip part is stiff, the tip part may damage the blood vessel. In addition, in case of the liver, the difference between the maximum and minimum diameters of blood vessels which should be passed through by a micro guidewire is approximately 5-6 times, and a steered tip shape having a tip part angle of at least approximately 180 degrees should be achieved, which is not easy to achieve.

Referring to (c) of FIG. 5, in order to solve the problem of (b), a single bending shape which may pass through a small blood vessel may be considered. However, in this case, since it is impossible to reach an entrance of a desired blood vessel from a large blood vessel, a problem occurs in which selective insertion is impossible.

Referring to (d) of FIG. 5, illustrated is a method in which an intermediate length is selected between a large length in (b) and a short length in (c) as the length L of a portion steered by a combined method of (b) and (c). In this case, in a small blood vessel, the bending radius of a steered tip shape is required to be the same as that in (b) of FIG. 5, but the length L is decreased and deformation may be reduced. However, in order to reach the entrance of a blood vessel from a large blood vessel, the angle increases by which the tip part comes into contact with a blood vessel wall, and since the larger, the better the angle, a large angle does not cause a problem, but insertion becomes difficult because Lx becomes greater than Ly.

The limitation of the single bending described in (b) to (d) of FIG. 5 may be solved by a two-stage bent shape.

Referring to (e) of FIG. 5, when a steerable tip part has a two-stage bent shape, the conditions of $\theta_{contact}$, and Lx and Ly may all be satisfied, and even in a section of a small length of the steerable tip part, the conditions of $\theta_{contact}$, and Lx and Ly are satisfied, and thus, it may be understood that selective insertion is possible even in a small blood vessel without additional bending.

In addition, since the end of the steerable tip part may reach a desired blood vessel, Lx should be larger than the blood vessel diameter $D_{vessel}$ as in following Equation 3.

$$Lx > D_{vessel} \quad \text{[Equation 3]}$$

Thus, the present invention proposes a steerable guidewire having a two-stage bending radius.

FIG. 6 is a view illustrating a structure of a steerable guidewire in accordance with an exemplary embodiment of the present invention.

Referring to (a) and (b) of FIG. 6, a steerable guidewire 200 according to an exemplary embodiment of the present invention may include a steerable tip part 210 which is steerable and a non-steerable tip part 220 which is connected to the steerable tip part 210 and is not steerable, and the steerable tip part 210 may be divided into a first steerable tip part 211 and a second steerable tip part 212 so as to have a two-stage bent shape.

At this point, the steerable tip part 210 may be divided into N portions so as to have N-stage bent shape.

In order to actively steer the tip part of the steerable guidewire, various techniques have been developed. These techniques may be divided, according to a steering mechanism, into a magnetic induction type, a wire type, a shape memory alloy type, an electrically activated polymer type, a pressure type, and the like.

Referring to (c) of FIG. 6, a steerable guidewire 200 according to an exemplary embodiment of the present invention may further include, unlike (a) of FIG. 6, at least one different steerable tip part 210' positioned between the steerable tip part 210 and the non-steerable tip part 220.

FIG. 7 is a view for describing a steering mechanism using magnetic induction.

Referring to FIG. 7, a magnetic induction type is constituted by: a permanent magnet fixed to the tip part of a steerable catheter or a guidewire; and a magnetic field system which generates a magnetic field on the outside. For example, as shown in (a) of FIG. 7, when generating a magnetic field, which passes though a patient, by an external magnetic field system, the permanent magnet fixed to the catheter tip part receives a torque by the magnetic field and is steered in a desired direction. External force applied to the permanent magnet fixed to the tip part is a single-degree-of-freedom torque, and thus, one among the position and the angle of the tip part may be controlled by a single magnetic field vector.

Representative steerable catheter systems of the magnetic induction type include a Niobe system developed by Stereotaxis Co in (b), and a CGCI system developed by Magnetecs Co. in (c). In case of the magnetic induction type, when only a small permanent magnet is positioned at the tip part of the catheter and the guidewire, steering is possible by using an external magnetic field, and there is a merit of easy miniaturization, but in case of the systems of (b) and (c), each system has a limit in a steering degree of freedom.

(b) of FIG. 7 shows a magnetic induction-type steerable catheter system developed by Streotaxis Co., and since a strong magnetic field is required to steer a small permanent magnet inside a patient, a large permanent magnet is located on the outside. However, for the miniaturization of the catheter, the smaller the permanent magnet is used at the tip part, the larger the magnetic field is required and the larger the size of the external permanent magnet. Thus, the orientation range of the magnetic field which may be generated by moving the external permanent magnet is decreased and the steerable angle is limited. In addition, since only a single-direction magnetic field may be generated by a pair of external permanent magnets, it is difficult to achieve multiple degrees of freedom to make various bending of the catheter or the guidewire even when the number of permanent magnets is increased at the tip part.

(c) of FIG. 7 shows a CGCI system developed by Magnetecs Co. and four pairs of coils, that is, eight coils ware used instead of a permanent magnet. Unlike the Niobe system in which a magnetic field is generated by physically moving a permanent magnet, magnetic fields having all orientations may be achieved because a magnetic field vector is generated by adjusting the currents of the four pairs of coils. However, the four magnetic fields generated by the four pairs of coils are consequently a single vector having a size and a direction inside a patient. Therefore, even when increasing the number of permanent magnets at the tip part, the same problem occurs in which it is difficult to achieve multiple degrees of freedom to make various bending of the catheter or the guidewire.

FIG. 8 is a view for describing a steering mechanism using a wire.

Referring to FIG. 8, a steerable catheter or guidewire of a wire-driving type is constituted by; a structure which may easily be bent; and a wire which passes through the inside of the structure and is fixed to a tip part. As shown in (a) of FIG. 8, since the wire is fixed to the tip part, when the wire is pulled from the outside, the total structure is steered in the direction of the wire while being bent. According to the shape of a bent structure, the number of wires, and the position at which the wire is fixed, a degree of freedom may be variously achieved from a single degree of freedom to multiple degrees of freedom and various bent shapes may be formed. However, each of the wires should have sufficient thickness so as to be capable of withstanding repeated stress against tension, and since an internal shape for bending is also not simple, the miniaturizable size is limited.

FIG. 9 is a view for describing a steering mechanism using a shape memory alloy.

Referring to FIG. 9, a steerable catheter or guidewire using a shape memory alloy uses the characteristics of the shape memory alloy which is deformed due to temperatures. As shown in (a) and (b) of FIG. 9, steering is achieved by arranging a coil-shaped shape memory alloy inside a catheter and using a change in length due to temperatures, or as shown in (c) of FIG. 9, steering may be achieved by making a shape memory alloy into a specific structure and increasing the deformation in a specific direction. However, since an internal structure for steering is not simple and heat insulation is required according to a principle of driving by temperatures, a miniaturizable size is limited when considering up to heat insulation. In addition, there is a limitation in that consideration of safety is also required due to an operation at a high temperature.

FIG. 10 is a view for describing a steering mechanism using an electrically activated polymer.

Referring to FIG. 10, a steerable catheter or guidewire using an electrically activated polymer uses the characteristics of an electrically activated polymer which has a shape varying according to voltages. As shown in (a) of FIG. 10, when applying a voltage after joining a general material which is not affected by a voltage and an electrically activated polymer, bending may be achieved by a difference in deformation of the two materials. In addition, as shown in (b) of FIG. 10, multiple-degree-of-freedom bending may be achieved through a method of applying a voltage only to an electrode of a portion at which multiple electrodes are arranged and bending is to be achieved. However, in order to transmit a voltage up to a tip part, a long electric wire which is strong against repeated bending should be connected, and the inside and outside of the wire and the electrode should be insulated. Therefore, as a degree of freedom increases, the miniaturizable size is limited. In addition, there is a limitation in that consideration of safety is also required due to an operation at a high voltage.

FIG. 11 is a view for describing a steering mechanism using pressure.

Referring to FIG. 11, a steerable catheter or guidewire using pressure is constituted by: a non-symmetrical structure of a tip part; and an inner tube which may apply a pressure to the tip part. When the structure is non-symmetric, deformation becomes non-symmetric when applying an internal pressure, bending may be achieved, and multiple degrees of freedom may be achieved by dividing the inside into several sections. In (a) of FIG. 11, the inside is divided into three sections, and three-directional bending is achieved by applying a pressure to each section, and in (b) of FIG. 11, multiple segments are formed and steering is achieved by using a band pass valve when pressures are different from each other in respective segments. In case of a pressure-driven mechanism, an independent tube for pressure transmission should be connected for each degree of freedom, and thus, as the degree of freedom increases, a miniaturizable size is limited.

A steerable guidewire having a two-stage bending shape according to an embodiment may be applied to a magnetic induction type, a wire type, a shape memory alloy type, an electrically activated polymer type, a pressure type, and the like, and a case of application to the pressure type will be hereinafter described as an example.

FIG. 12 is a view illustrating a steerable guidewire using pressure in accordance with an exemplary embodiment of the present invention.

As shown in FIG. 12, a steerable guidewire 200 using pressure according to an exemplary embodiment of the present invention may include: a steerable tip part 210; a non-steerable tip part 220 connected to the steerable tip part 210; and a pressure transmission part 230 connected to the non-steerable tip part 220.

The steerable tip part 210 may be bent in two stages by an internal pressure. That is, the steerable tip part 210 may be bent in two stages by a pressure applied once. Such the steerable tip part 210 may be formed of, for example, medical silicone.

The pressure transmission part 230 is the stiffest and may transmit a pressure through an internal tube.

The non-steerable tip part 220 has one end connected to the steerable tip part 210 and the other end connected to the pressure transmission part 230, and may connect the stiff pressure transmission part and the non-steerable tip part 220. The non-steerable tip part 220 may be formed of, for example, stainless steel.

At this point, the pressure transmission part 230 has the largest length and occupies most of the steerable guidewire, and the steerable tip part 210 and the non-steerable tip part 220 have relatively small lengths. Such the pressure transmission part 230 may include a first tube formed of, for example, stainless steel and a second tube which surrounds the first tube and is formed of PEBAX.

FIG. 13 is a view illustrating a specific structure of the steerable tip part shown in FIG. 12.

Referring to FIG. 13, a steerable tip part 210 according to an embodiment may be formed in a tube or pipe shape, and be divided into a first steerable tip part 211 and a second steerable tip part 212 so as to achieve at least two-stage bending in a single degree of freedom by a pressure mechanism. At this point, the cross-section of the tube or pipe is not limited to a circular shape.

In order to achieve the two-stage bending by an internal pressure, the steerable tip part 210 has a pattern formed therein with eccentricity. The steerable tip part 210 has a pattern formed in a non-symmetrical structure with respect to a center axis line A in order to achieve a bent shape, and is formed in a non-symmetrical structure which is not constant even in the lengthwise direction, in order to achieve a bent shape of two or more stages, that is, in at least two different structures. The steerable tip part 210 may have a structure of two or more stages, and the length of the first steerable tip part 211 which is the farthest end portion should be smaller than approximately two times of the minimum diameter of a blood vessel in which the steerable tip part is to be inserted.

In the steerable tip part 210, the distance a from the center axis line A to a first inner circumferential surface may be formed to be larger than the distance b from the center axis line A to a second inner circumferential surface. In addition, in the steerable tip part 210, with respect to the center axis line A, the thickness $\alpha$ at the first inner circumferential surface may be formed to be smaller than the thickness $\beta$ at the second inner circumferential surface facing the first inner circumferential surface.

FIG. 14 is a view illustrating a specific structure of the non-steerable tip part shown in FIG. 12.

Referring to FIG. 14, the non-steerable tip part is a portion which connects the relatively soft steerable tip part and the relatively stiff pressure transmission part. While a guidewire is inserted into a blood vessel, and a change in bending stiffness is rapid when pushing the guidewire into the blood vessel even though the steerable tip part of the guidewire enters in the direction of a desired blood vessel, a problem occurs in which the guidewire may not enter following the steerable tip part. That is, as shown in (a) of FIG. 14, an internal force F acting on the guidewire is the same, and when bending stiffness k2 is too smaller than K1, x1 becomes smaller than x2 and thus the guidewire may not follow the steerable tip part.

As shown in (b) of FIG. 14, bending stiffness may be reinforced by a coil so that bending stiffness gradually increases from the steerable tip part to the pressure transmission part. That is, the non-steerable tip part may have one or more coils positioned therein, wherein the one or more coils may each have an increasing pitch (or interval), increasing diameter, or simultaneously increasing pitch and diameter. Here, the non-steerable tip part is divided into three sections, coil groups each including a plurality of coils are located at the respective sections, each of the plurality of coil groups have a plurality of coils having the same diameter for each group and arranged so as to have mutually different intervals, and the diameters of the plurality of coils may be different for each group. A case is shown as an example, which is configured such that the coils having the smallest first diameter are arranged so as to have gradually increasing intervals therebetween in a first section A, the coils having the larger second diameter than the first diameter are arranged so as to have gradually increasing intervals therebetween in a second section B, and the coils having the larger third diameter than the second diameter are arranged so as to have gradually increasing intervals therebetween in a third section C, and thus, bending stiffness gradually increases from the steerable tip part.

Although not shown, in another example, the non-steerable tip part has therein a plurality of coils having a predetermined diameter and arranged at predetermined intervals, and the predetermined diameter and the predetermined interval may be changed. That is, the non-steerable tip part may be formed in a structure in which a plurality of coils having a predetermined diameter are arranged at predetermined intervals without being divided into a plurality of sections, and the diameter and the interval simultaneously increase as being farther from the steerable tip part. Of course, the non-steerable tip part is not limited to the example described herein, but may be implemented in various forms.

The bending stiffness of such coils increases as the second cross-sectional moment of inertia increases, and increases as the pitch which is the interval between the coils increases. Therefore, the coil may be designed so that the bending stiffness thereof gradually increases by adjusting the corresponding dimensions. In order to insert the non-steerable tip part into a desired blood vessel, the ratio of k1 and k2 is important. Therefore, it is ideal for bending stiffness to linearly increase in a log scale, and to this end, it is important to determine the pitch of the coil and the second cross-sectional moment of inertia of the wire.

FIG. 15 is a view illustrating a method for manufacturing a steerable guidewire in accordance with an exemplary embodiment of the present invention, and FIG. 16 is a view for describing steps for manufacturing the steerable guidewire of FIG. 15.

Referring to FIG. 15, a method for manufacturing a steerable guidewire according to an exemplary embodiment of the present invention may include a pattern formation step S100, a coating section formation step S200, a coating body formation step S300, and a guidewire formation step S400. In addition, the steerable catheter described with reference to FIG. 3 may also be manufactured through the same method as the above.

1) In the pattern formation step S100, a pattern may be formed on one side of a cylindrical template. As shown in (a) of FIG. 16, a cylindrical template 10 is prepared, and as shown in (b) and (c) of FIG. 16, an engraved pattern corresponding to an inner pattern is formed on one side of the template 10 by using a stamp 20 on which a predetermined embossed pattern 20a is formed. Thus, a template 10' on which the engraved pattern is formed may be formed. At this point, the template should be physically deformable, and a solvent should be present which may selectively dissolve the template without affecting the material of the steerable tip part. A material for the template may be, for example, ABS plastic. The ABS plastic is the abbreviation for acrylonitrile butadiene styrene, and has styrene as a main material among the three materials.

At this point, the predetermined embossed pattern may have, for example, an inverted triangle-shaped cross-section, and the reason for this is because the template may easily be separated not until the contact area between the pattern and the template is reduced.

2) In the coating section formation step S200, as shown in (d) of FIG. 16, the outer circumferential surface of the template 10' on which the engraved pattern is formed by using a micro mold is coated with a flexible material 30, and thus, the coating section 40 may be formed. The flexible material may be polydimethylsiloxane (PDMS).

3) In the coating body formation step S300, the coating section is cured, so that the coating body including the template on which the engraved pattern is formed and the coating body including the coating section may be formed. At this point, the coating section coated on the template on which the engraved pattern is formed may be cured by heating or natural curing.

4) In the guidewire formation step S400, as shown in (e) of FIG. 16, the template on which the engraved pattern is formed is removed from the coating body, so that a steerable guidewire may be formed. At this point, in the present invention, the template on which the engraved pattern is formed may be removed from the coating body by using a predetermined solvent. Here, the predetermined solvent may be, for example, acetone which dissolves the template formed of ABS plastic and does not dissolve the coating part formed of a PDMS resin, but the embodiment of the present invention is not limited thereto.

The steerable catheter may also be manufactured through the same method as described above. A method for manufacturing the steering catheter may include the following steps. A pattern formation step for forming an engraved pattern on one side of a cylindrical template using a stamp on which a predetermined embossed pattern is formed; a coating section formation step for forming a coating section by coating, with a flexible material, an outer circumferential surface of the template on which the engraved pattern is formed; a coating body formation step for curing the coating section and forming a coating body including the template on which the engraved pattern is formed and the coating section; and a catheter formation step for removing, from the coating body, the template on which the engraved pattern is formed to form a steerable catheter.

As such, according to the present invention, the steerable tip part of a guidewire or a catheter is deformed in a bent shape of at least two stages, is steered in a predetermined direction, and thus may be selectively inserted into a blood vessel in a desired direction and improve a steering performance.

In addition, according to the present invention, the selective insertion may be performed for all blood vessels from large-diameter blood vessels to small-diameter blood vessels.

In addition, according to the present invention, since the steerable tip part is deformed in a bent shape of at least two stages and steered in a predetermined direction, the steerable tip part may be applied not only to a single-degree-of-freedom guidewire or catheter, but also to a multiple-degree-of-freedom guidewire or catheter.

In addition, according to the present invention, since deformation in a bent shape of at least two stages and steering is possible at a single degree of freedom, an internal structure for steering is simple and may be miniaturized.

In addition, the present invention may be applied to all steering mechanisms that use various methods, such as magnetic induction, wires, shape memory alloys, electrically activated polymers or pressures. However, the purpose of the present invention is not limited the above purposes, and may be variously expanded without departing from the spirit and scope of the present invention.

Features, structures, and effects described in the above embodiments are incorporated into at least one embodiment of the present disclosure, but are not limited to only one embodiment. Moreover, features, structures, and effects exemplified in one embodiment can easily be combined and modified for another embodiment by those skilled in the art. Therefore, these combinations and modifications should be construed as falling within the scope of the present disclosure.

In addition, although embodiments have mainly been described, it will be understood that the embodiments do not limit the present invention, and various modifications and applications that are not exemplified so far may be devised by those skilled in the art without departing from fundamental characteristics of the embodiments. For example, each of components specifically described in examples may be implemented with modification. In addition, differences related to variations and modifications should be construed to be within the scope of the present invention defined in appended claims.

What is claimed is:

1. A steerable guidewire, which is inserted into a catheter and guides the catheter to a desired blood vessel, the steerable guidewire comprising:
    a steerable tip part that can be bent in at least two stages due to an external stimulus and that is steered in a predetermined direction such that an end of the steerable guidewire is steerable; and
    a non-steerable tip part that is not steerable, wherein:
    the steerable tip part comprises
        a first steerable tip part having a first length and bent in a first angle with respect to the non-steerable tip part, and
        a second steerable tip part having one end connected to the first steerable tip part, having a second length, and bent and steered into a second angle with respect to the non-steerable tip part;
    the first steerable tip part is positioned farther from the non-steerable tip part than the second steerable tip part; and
    the first length of the first steerable tip part is smaller than a sum of lengths of steerable tip parts other than the first steerable tip part, and the first angle is steered so as to be larger than the second angle, wherein
    the steerable tip part has a tubular shape and is formed in a non-symmetrical structure with respect to a center axis line of the inside thereof, and
    in the steerable tip part, a distance from the center axis line to a first inner circumferential surface is larger than a distance from the center axis line to a second inner circumferential surface facing the first inner circumferential surface.

2. The steerable guidewire of claim 1, wherein the steerable tip part has a single degree of freedom and is bent in a bent shape of at least two stages.

3. The steerable guidewire of claim 2, wherein the steerable tip part is steered in shapes of Equations 1, 2, and 3 below:

$$\theta_{tip} > \theta_{vessel} - 90 \qquad \text{[Equation 1]}$$

$$Ly > Lx \qquad \text{[Equation 2]}$$

$$Lx > D_{vessel}, \qquad \text{[Equation 3]}$$

where Lx, Ly are lengths of the steerable guidewire in an x-direction and a y-direction with respect to a bent section from one end to the other end of the steerable tip part, $\theta_{tip}$ is an angle of an end, that is, the other end of the steerable guidewire, and $D_{vessel}$ is a diameter of a blood vessel.

4. The steerable guidewire of claim 1, wherein the steerable tip part is formed in at least two different structures in a lengthwise direction.

5. The steerable guidewire of claim 1, wherein the second steerable tip part has a predetermined pattern form on one side therein.

6. The steerable guidewire of claim 1, wherein the non-steerable tip part has a bending stiffness that gradually increases from the steerable tip part.

7. The steerable guidewire of claim 6, wherein the non-steerable tip part has one or more coils positioned therein, the one or more coils each having an increasing pitch, increasing diameter, or a simultaneously increasing pitch and diameter.

8. The steerable guidewire of claim 1, wherein the end of the steerable guidewire can be bent due to the external stimulus and is steered in the predetermined direction.

9. A steerable guidewire, which is inserted into a catheter and guides the catheter to a desired blood vessel, comprising:
    a steerable tip part that can be bent in at least two stages due to an external stimulus and that is steered in a predetermined direction such that an end of the steerable guidewire is steerable; and
    a non-steerable tip part that is not steerable, wherein:
    the steerable tip part comprises
        a first steerable tip part having a first length and bent so as to have a first bending radius, and
        a second steerable tip part having one end connected to the first steerable tip part and the other end connected to the non-steerable tip part, having a second length, and bent and steered so as to have a second bending radius;
    the first steerable tip part is positioned farther from the non-steerable tip part than the second steerable tip part;
    the first length is smaller than a second length, and the first bending radius is smaller than the second bending radius;
    the steerable tip part has a tubular shape and is formed in a non-symmetrical structure with respect to a center axis line of the inside thereof; and
    in the steerable tip part, a distance from the center axis line to a first inner circumferential surface is larger than a distance from the center axis line to a second inner circumferential surface facing the first inner circumferential surface.

10. The steerable guidewire of claim 9, wherein the steerable tip part has a single degree of freedom and is bent in a bent shape of at least two stages.

11. The steerable guidewire of claim 10, wherein the steerable tip part is steered in shapes of Equations 1, 2, and 3 below:

$$\theta_{tip} > \theta_{vessel} - 90 \qquad \text{[Equation 1]}$$

$$Ly > Lx \qquad \text{[Equation 2]}$$

$$Lx > D_{vessel}, \qquad \text{[Equation 3]}$$

where Lx, Ly are lengths of the steerable guidewire in an x-direction and a y-direction with respect to a bent section from one end to the other end of the steerable tip part, $\theta_{tip}$ is an angle of an end, that is, the other end of the steerable guidewire, and $D_{vessel}$ is a diameter of a blood vessel.

12. A steerable catheter comprising:
a steerable tip part that can be bent in at least two stages due to an external stimulus and that is steered in a predetermined direction such that an end of the steerable guidewire is steerable; and
a non-steerable tip part that is not steerable, wherein:
the steerable tip part comprises
    a first steerable tip part having a first length and bent in a first angle with respect to the non-steerable tip part, and
    a second steerable tip part having one end connected to the first steerable tip part, having a second length, and bent and steered into a second angle with respect to the non-steerable tip part;
the first steerable tip part is positioned farther from the non-steerable tip part than the second steerable tip part;
the first length of the first steerable tip part is smaller than a sum of lengths of steerable tip parts other than the first steerable tip part, and the first angle is steered so as to be larger than the second angle;
the steerable tip part has a tubular shape and is formed in a non-symmetrical structure with respect to a center axis line of the inside thereof; and
in the steerable tip part, a distance from the center axis line to a first inner circumferential surface is larger than a distance from the center axis line to a second inner circumferential surface facing the first inner circumferential surface.

13. The steerable catheter of claim 12, wherein the steerable tip part has a single degree of freedom and is bent in a bent shape of at least two stages.

14. The steerable catheter of claim 13, wherein the steerable tip part is steered in shapes of Equations 1, 2, and 3 below:

$$\theta_{tip} > \theta_{vessel} - 90 \quad \text{[Equation 1]}$$

$$Ly > Lx \quad \text{[Equation 2]}$$

$$Lx > D_{vessel}, \quad \text{[Equation 3]}$$

where $Lx$, $Ly$ are lengths of the steerable guidewire in an x-direction and a y-direction with respect to a bent section from one end to the other end of the steerable tip part, $\theta_{tip}$ is an angle of an end, that is, the other end of the steerable guidewire, and $D_{vessel}$ is a diameter of a blood vessel.

* * * * *